United States Patent [19]

Scott

[11] Patent Number: 5,270,329
[45] Date of Patent: Dec. 14, 1993

[54] ANTITUMOR COMPOSITIONS AND METHODS OF TREATMENT

[75] Inventor: William L. Scott, Indianapolis, Ind.

[73] Assignee: Eli Lilly and Company, Indianapolis, Ind.

[21] Appl. No.: 988,543

[22] Filed: Dec. 10, 1992

[51] Int. Cl.$^5$ ............... A61K 31/415; C07D 233/40; C07D 407/12

[52] U.S. Cl. ............... 514/392; 548/311.4; 548/316.7; 548/312.1

[58] Field of Search ............ 548/311.4, 316.7, 312.1; 514/392

[56] References Cited

U.S. PATENT DOCUMENTS

| | | | |
|---|---|---|---|
| 3,097,242 | 7/1963 | Hoehn et al. | 514/592 |
| 3,102,115 | 8/1963 | Breuer et al. | 514/592 |
| 3,102,121 | 8/1963 | Breuer et al. | 514/415 |
| 3,736,122 | 5/1973 | Tung et al. | 514/592 |
| 3,849,110 | 11/1974 | Soper et al. | 514/592 |
| 4,173,645 | 11/1979 | Enders et al. | 514/392 |
| 4,389,401 | 6/1983 | Smolanoff | 514/392 |
| 4,591,597 | 5/1986 | Schweizer | 514/392 |
| 4,845,128 | 7/1989 | Harper et al. | 514/592 |
| 5,169,860 | 12/1992 | Mohamadi et al. | 514/415 |

FOREIGN PATENT DOCUMENTS

| | | |
|---|---|---|
| 1208561 | 7/1986 | Canada . |
| 107214 | 9/1983 | European Pat. Off. . |
| 166615 | 1/1986 | European Pat. Off. . |
| 222475 | 5/1987 | European Pat. Off. . |
| 1144259 | 2/1963 | Fed. Rep. of Germany . |
| 505106 | 5/1971 | Switzerland . |
| 2127820 | 4/1984 | United Kingdom . |

OTHER PUBLICATIONS

W. J. Ehlhardt, *Drug Metabolism and Disposition*, 19:370 (1991).
J. J. Howbert, et al., *Synthetic Communications*, 20:3193 (1990).
W. J. Ehlhardt, *Drug Metabolism and Disposition*, 19:366 (1991).
J. J. Howbert, et al., *Journal of Medicinal Chemistry*, 33:2393 (1990).
G. B. Grindey, et al., *Proceedings of the American Association of Cancer Research*, 27:277 (Abstract 1099) (1986).
C. W. Taylor, et al., *Journal of Clinical Oncology*, 7:1733 (1989).
J. D. Hainsworth, et al., *Cancer Research*, 49:5217 (1989).
R. Levine, *Diabetes Care*, 7 (Suppl. 1):3–7 (1984).
G. F. Holland, et al., *Journal of Medicinal and Pharmaceutical Chemistry*, 3:99 (1961).
P. J. Houghton, et al., *Cancer Chemotherapy and Pharmacology*, 25:84 (1989).
P. J. Houghton, et al., *Cancer Research*, 50:318 (1990).
P. J. Houghton, et al., *Cancer Research*, 50:664 (1990).
P. J. Houghton, et al., *Biochemical Pharmacology*, 39:1187 (1990).
P. H. Dhahir, et al., In *Proceedings of the 36th ASMS Conference on Mass Spectroscopy and Allied Topics*, pp. 972–973 (1988).
G. F. Holland, *Journal of Organic Chemistry*, 26:1662 (1961).
*Chemical Abstracts*, 52:17180; citing Haack, et al., East German Patent 9688, Apr. 21, 1955.
F. Kurzer, *Chemical Reviews*, 50:1 (1952).
G. B. Grindey, et al., In *Proceedings of the American Association for Cancer Research*, 28:309 (Abstract 1224) (1987).
H. Breuer, et al., *Chimie Therapeutique*, Nov./Dec. 1973:659.
L. J. Lerner, et al., *Metabolism*, 14:578 (1965).
T. L. Hough, et al., *Journal of Heterocyclic Chemistry*, 23:1125–1130 (1986).

*Primary Examiner*—Joseph Paul Brust
*Assistant Examiner*—Mary Susan H. Gabilan
*Attorney, Agent, or Firm*—Paul J. Gaylo; Leroy Whitaker

[57] ABSTRACT

This invention provides the use of certain tetra-substituted imidazolidin-2-one derivatives in the treatment of susceptible neoplasms in mammals. Also provided are certain novel tetra-substituted imidazolidin-2-one derivatives and pharmaceutical formulations employing them.

15 Claims, No Drawings

ANTITUMOR COMPOSITIONS AND METHODS OF TREATMENT

BACKGROUND OF THE INVENTION

In recent years fundamental advances have been made in the development of chemical agents and regimens of therapy to combat neoplastic diseases. Despite these continuing advances, cancers continue to exact intolerable levels of human pain and suffering. The need for new and better methods of treating neoplasms and leukemias continues to fuel efforts to create new classes of compounds, especially in the area of inoperable or metastatic solid tumors, such as the various forms of lung cancer. Of the one million new cases of cancer diagnosed in the United States each year, more than 90% represent non-hematopoetic tumors, where improvements in five-year survival rates have been modest, at best. B. E. Henderson, et al., *Science*, 254:1131–1137 (1991).

The recent avalanche of information regarding the basic biological processes involved in neoplasms has led to a deeper understanding of the heterogeneity of tumors. Ongoing work has led to the realization that individual tumors may contain many subpopulations of neoplastic cells that differ in crucial characteristics such as karyotype, morphology, immunogenicity, growth rate, capacity to metastasize, and response to antineoplastic agents.

It is because of this extreme heterogeneity among populations of neoplastic cells that new chemotherapeutic agents should have a wide spectrum of activity and a large therapeutic index. In addition, such agents must be chemically stable and compatible with other agents. It is also important that any chemotherapeutic regimen be as convenient and painless as possible to the patient.

This invention reports a new series of tetra-substituted imidazolidin-2-ones. These new imidazolidin-2-ones are useful in the treatment of solid tumors. These compounds are orally active—which, of course, results in less trauma to the patient—and are relatively non-toxic. These compounds also have an excellent therapeutic index.

The tetra-substituted imidazolidin-2-ones of this invention are derivatives of various diarylsulfonylureas. Many such sulfonylureas are known in the art. Certain of these compounds are known to have hypoglycemic activities, and have been used medicinally as such agents. In addition, sulfonylureas have been taught to have herbicidal and antimycotic activities. General reviews of compounds of this structural type are taught by Kurzer, *Chemical Reviews*, 50:1 (1952) and C. R. Kahn and Y. Shechter, *Goodman and Gilman's, The Pharmacological Basis of Therapeutics*, (Gilman, et al., 8th ed. 1990) 1484–1487. Some diarylsulfonylureas have been reported as being active antitumor agents. e.g., U.S. Pat. No. 4,845,128 of Harper, et al., issued Jul. 4, 1989; U.S. Pat. No. 5,110,830 of Harper, et al.. issued May 5, 1992; U.S. Pat. No. 5,116,874 of G. A. Poore, issued May 26, 1992; U.S. Pat. No. 5,169,860 of Mohamadi, et al., issued Dec. 8, 1992; European Patent Publication 0467613 (published Jan. 22, 1992); Grindey, et al., *American Association of Cancer Research*, 27:277 (1986); and Houghton, et al., *Cancer Chemotherapy and Pharmacology*, 25:84–88 (1989).

SUMMARY OF THE INVENTION

This invention provides a method of treating susceptible neoplasms in mammals which comprises administering to a mammal in need of said treatment an oncolytically effective amount of a compound of Formula I:

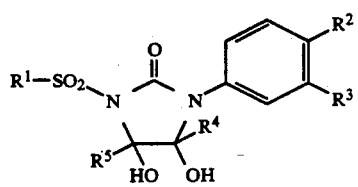

wherein: $R^1$ is selected from the group consisting of

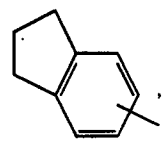

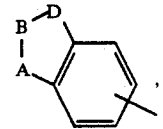

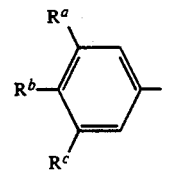

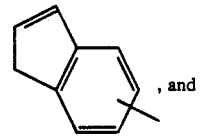

, and

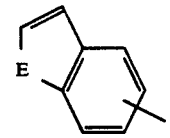

wherein
E is nitrogen, sulfur, or oxygen;
wherein A is —O—, —S(O)$_n$—, —CH$_2$S(O)$_n$—, —NR—, —CH$_2$—, —CH$_2$CH$_2$—, or —CH$_2$O—;
D is —CH$_2$—, —S(O)$_n$—, —NR—, —CH$_2$S(O)$_n$—, or —O—;
B is —CH$_2$—, —O—, —S(O)$_n$—, or —NR—;
R is methyl or ethyl;
n is 0–2;
provided that at least one of A, B, and D is not —S(O)$_n$— or —CH$_2$S(O)$_n$—; and
$R^a$, $R^b$, and $R^c$ are independently selected from the group consisting of hydrogen, halo, $C_1$–$C_3$ alkyl, $C_1$–$C_3$ alkoxy, and trifluoromethyl;
$R^4$ and $R^5$ are independently selected from the group consisting of hydrogen and $C_1$–$C_3$ alkyl;

$R^3$ is hydrogen, halo, $C_1$-$C_3$ alkyl, or trifluoromethyl; and $R^2$ is halo, $C_1$-$C_3$ alkyl, or trifluoromethyl; or a pharmaceutically acceptable salt or solvate thereof.

This invention also provides novel compounds of Formula I and pharmaceutical formulations comprising an effective amount of a compound of Formula I in combination with a suitable pharmaceutical carrier, diluent, or excipient. These compounds and formulations are useful in the treatment of mammals suffering from susceptible neoplasms.

DETAILED DESCRIPTION AND PREFERRED EMBODIMENTS

As used herein, the term "halo" refers to fluoro, chloro, bromo, and iodo.

Preferred compounds of the instant invention are those of Formula I wherein:

$R^1$ is selected from the group consisting of 2,3-dihydrobenzofuryl, indanyl, indenyl, benzofuryl, indolyl, indolinyl, halo-substituted phenyl, and alkyl-substituted phenyl;

$R^2$ is chloro, bromo, methyl, or trifluoromethyl;

$R^3$ is hydrogen, chloro, bromo, methyl, or trifluoromethyl; and $R^4$ and $R^5$ are independently hydrogen or methyl.

The compounds of formula I can be prepared by methods known in the literature. Usually the compounds of Formula I are synthesized by first preparing the cognate sulfonylurea of Formula II

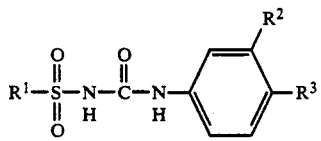

wherein $R^1$, $R^2$ and $R^3$ are as defined supra. The sulfonylureas of Formula II can be prepared by any number of methods known in the literature. Generally, these methods involve either the reaction of a sulfonamide with an isocyanate or a reaction of a sulfonylcarbamate with an appropriately-substituted aniline.

A preferred process for preparing a compound of Formula II comprises reacting a sulfonylisocyanate of Formula III

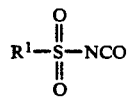

with an aniline derivative of Formula IV

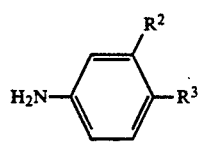

wherein $R^1$, $R^2$, and $R^3$ are the same as previously defined, generally in the presence of a base. Any suitable basic material, such as sodium hydroxide, potassium hydroxide, lithium hydroxide, sodium methoxide, sodium hydride and the like, can be used.

The reaction between compounds III and IV is usually performed using equimolar amounts of the two reactants, although other ratios are operative. The reaction is preferably carried out in a solvent which is non-reactive under the reaction conditions such as benzene, toluene, acetonitrile, diethyl ether, tetrahydrofuran, dioxane, methylene chloride, or most preferably acetone.

The reaction can be carried out at temperatures from about 0° C. up to about 100° C. At the preferred temperature range of from about 20° C. to about 30° C., the reaction produces a strong exotherm and the reaction is usually complete within one hour. The product thus obtained can be recovered by filtration and can be purified, if desired, by any number of methods known to those skilled in the art, such as chromatography or crystallization.

An alternative process for preparing a compound of Formula II comprises reacting an appropriately substituted sulfonamide of Formula V

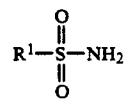

with an isocyanate of Formula VI

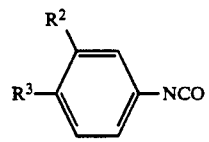

to provide the corresponding compound of Formula II.

The reaction is generally performed in a mixture of water and a water-miscible, non-reactive solvent such as tetrahydrofuran or acetone in the presence of an acid scavenger such as sodium hydroxide, potassium hydroxide, lithium hydroxide, sodium methoxide, sodium hydride and the like. Generally, an equimolar or slight molar excess of VI is employed, although other ratios are operative. Usually, the amount of base used is approximately equimolar to the amount of V. The reaction is generally carried out from about 0° C. up to about 100° C. At the preferred temperature of about 20° C. to about 30° C., the reaction is usually complete within about three hours.

A preferred process for preparing a compound of Formula II involves reacting a sulfonamide of Formula V with an alkyl haloformate of the formula $XCOOR^9$, where X is bromo or chloro and $R^9$ is $C_1$-$C_3$ alkyl, to provide the carbamate of Formula VII and then reacting it with an aniline derivative of Formula IV to provide the corresponding product I

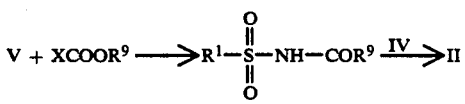

The transformation of V into VII is usually accomplished in a non-reactive solvent, such as acetone or methyl ethyl ketone, in the presence of an acid scavenger, such as an alkali metal carbonate, for example potassium carbonate. A molar excess of the haloformate is usually added, although other ratios are operative. The reaction mixture is heated to a temperature from about 30° C. up to the reflux temperature of the mixture for a period of about 1-6 hours to provide the desired intermediate VII. Intermediate carbamate VII and the substituted aniline IV are then heated together in an inert high-boiling solvent, such as dioxane, toluene, or diglyme, at temperatures from about 50° C. up to the reflux temperature of the mixture to provide the desired product I.

Intermediates II, IV, V, and VI and other reagents required for other methods of preparation, are commercially available, or can be prepared by methods known in the art. See, e.g. J. A. Aikins and E.V.P. Tao, European Patent Publication No. 254,577, published Jan. 27, 1988.

The sulfonylureas of Formula II are coverted into the tetra-substituted imidazolidin-2-ones of Formula I$^a$ or I$^b$ by reacting the sulfonylureas with pyruvaldehyde.

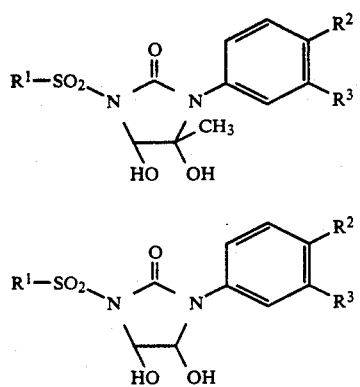

In addition, either Ia or Ib can consist of mixtures of alcohols in a cis or trans relationship to one another. It is believed that regioisomer I$^a$ predominates.

This invention also includes the pharmaceutically acceptable salts of the Formula I compounds. The Formula I compounds can react with basic materials such as alkali metal- or alkaline earth metal hydroxides, carbonates, and bicarbonates including, without limitation, sodium hydroxide, sodium carbonate, potassium hydroxide, calcium hydroxide, lithium hydroxide, etc. to form pharmaceutically acceptable salts such as the corresponding sodium, potassium, lithium, or calcium salt. Organic bases can also be used, including primary, secondary, and tertiary alkyl amines such as methylamine, triethylamine, and the like.

This invention further relates to the pharmaceutically acceptable solvates of the compounds of Formula I. The Formula I compounds can react with solvents such as water, methanol, ethanol and acetonitrile to form pharmaceutically acceptable solvates such as the corresponding hydrate, methanolate, ethanolate and acetonitrilate.

The terms and abbreviations used in the instant examples have their normal meanings unless otherwise designated. For example "°C." refers to degrees Celsius; "N" refers to normal or normality; "mmole" refers to millimole; "g" refers to gram; "ml" means milliliter; "M" refers to molar or molarity; and "NMR" refers to nuclear magnetic resonance.

The following examples further illustrate the preparation of the compounds of Formula I. These examples are illustrative only and are not intended to limit the scope of the invention in any way.

Preparation 1

Synthesis of N-[[(4-chlorophenyl)amino]-carbonyl]-indene-5-sulfonamide (A) and N-[[(4-chlorophenyl)amino]carbonyl]indene-6-sulfonamide (B)

A. Preparation of 1-Hydroxy-5-indanesulfonamide

To a stirred solution of 1-keto-5-indanesulfonamide (6.3 g, 30 mmol), in 120 ml of 50% aqueous methanol at 0° C. was added NaBH$_4$ (1.1 g, 30 mmol) in several portions. The cooling bath was removed and the mixture allowed to stir at room temperature for 30 minutes. After removal of the methanol in vacuo, the residue was extracted with ethyl acetate (4×75 ml) and the combined organic phase dried (Na$_2$SO$_4$). Filtration, followed by evaporation of the solvent, gave 5.4 g (84%) of product as a white solid.

B. Preparation of Indene-6-sulfonamide

A mixture of the product produced supra (3.07 g, 14.5 mmol) and p-toluenesulfonic acid monohydrate (276 mg, 1.5 mmol) in 1,2-dichloroethane (200 ml) was heated at reflux for 1 hour. After cooling, the solution was washed with 5% NaHCO$_3$ (1×100 ml) and water (1×100 ml) and dried (Na$_2$SO$_4$). Concentration in vacuo gave a yellow solid which was chromatographed on silica gel (20-40% EtOAc/hexane) to give 1.9 g (65%) of the product as a white solid.

C. Preparation of N-[[(4-chlorophenyl)amino]carbonyl]-indene-5-sulfonamide (A) and N-[[(4-chlorophenyl)amino]carbonyl]-indene-6-sulfonamide (B)

A solution of indene-6-sulfonamide (2.1 g, 10.8 mmol) in acetone (5 ml) and 1N aqueous NaOH (10.8 ml, 10.8 mmol) was treated dropwise with a solution of p-chlorophenylisocyanate (2.0 g, 12.8 mmol) in 5 ml acetone over 20 minutes. After stirring 2 hours, the insoluble bis(p-chlorophenyl)urea was removed by filtration and the resulting clear solution neutralized by the addition of 1N aqueous HCl (10.8 ml, 10.8 mmol). The slurry was stirred 30 minutes, filtered and washed with H$_2$O (100 ml) and ether (50 ml). Drying gave 3.4 g of solid, which was suspended in 100 ml of H$_2$O and treated with 1N aqueous NaOH (20 ml). The insoluble material was removed by filtration through a pad of Celite. Neutralization of the filtrate with 20 ml of 1N aqueous HCl precipitated a solid which was collected by filtration and dried to yield 2.21 g (59%) of the product. NMR studies indicated the product to be a 7:5 mixture of the 6- and 5-indenylsulfonyl isomers. These isomers may be separated, if desired, by techniques which are well known in the art.

Analysis of the product mixture gave the following results mp=159-161° C.; R$_f$ (1/9 MeOH/CHCl$_3$)=0.36; $^1$H NMR (300 MHz, d$_6$-DMSO) : A: δ 3.55 (s, 2H, CH$_2$), 6.90 (d, 1H, J=5.6 Hz, CH), 7.05 (m, 1H, CH), 7.25-7.35 (m, 4H, Ar-H), 7.60 (d, 1H, J=8.0 Hz, Ar-H), 7.84(d, 1H, J=8.0 Hz, Ar-H), 8.02 (s, 1H, Ar-H), 8.96 (bs, 1H, exchanges with D$_2$O, NH), 10.82 (bs, 1H, exchanges with D$_2$O, NH); B δ 3.52 (s, 2H, CH$_2$), 6.78 (d, 1H, J=5.6 Hz, CH), 7.05 (m, 1H, CH), 7.25-7.35 (m, 4H, Ar-H), 7.70 (d, 1H, J=8.0 Hz, Ar-H), 7.78 (d, 1H, J=8.0 Hz, Ar-H), 7.98 (s, 1H, Ar-H), 8.95 (bs, 1H, exchanges with D$_2$O, NH), 10.82

(bs, 1H, exchanges with D$_2$O, NH); IR(KBr) 3367, 3274, 1716, 1606, 1545, 1498, 1464, 1341, 1148, 1033, 922, 696 and 587 cm$^{-1}$; UV(EtOH) λmax(ε) 251.8 (29988) and 204.8 (37094) nm; FDMS (MeOH) m/e 348, 350 (M+).

Analysis for C$_{16}$H$_{13}$ClN$_2$O$_3$S:
Theory: C, 55.09; H, 3.76; N, 8.03.
Found: C, 55.19; H, 3.72; N, 7.84.

Preparation 2

Preparation of
N-[[(4-chlorophenyl)amino]carbonyl]-2-benzofuransulfonamide

To a solution of benzofuran (4.55 g, 38.5 mmol) in 100 ml of anhydrous tetrahydrofuran under a nitrogen atmosphere at −78° C. was added a 1.3M hexanes solution of n-butyllithium (29.6 ml, 38.5 mmol). The reaction was warmed to 0° C. and stirred for 30 minutes. Sulfur dioxide gas was bubbled through this mixture for 20 minutes at 0° C. and the reaction was concentrated under vacuum. The residue was dissolved in 100 ml of water, to which were added 304 millimoles of sodium acetate and 100 millimoles of hydroxylamine-O-sulphonic acid. This reaction was stirred at room temperature for 1.5 hours. The mixture was diluted with 200 ml of water, and the aqueous layer was separated and poured into 600 ml of diethyl ether. The ether layer was extracted with 1N sodium hydroxide (3×100 ml). The combined aqueous extract was acidified with about 300 ml of 1N hydrochloric acid, and then extracted with methylene chloride. The combined methylene chloride extract was dried with anhydrous sodium sulfate, filtered, and concentrated under vacuum to provide 2.3 g of 2-benzofuransulfonamide.

To a solution of sulfonamide (11.7 mmol) dissolved in 10 ml of acetone was added 1N aqueous sodium hydroxide (11.7 ml, 11.7 mmol). The mixture was stirred at room temperature for 10 minutes. A solution of the 4-chlorophenylisocyanate (11.7 mmol) dissolved in 10 ml of acetone was added dropwise to this mixture. The reaction was stirred overnight, then acidified with 11.7 ml (11.7 mmol) of 1N aqueous hydrochloric acid. The precipitated N-aryl-N'-arylsulfonylurea was filtered under vacuum and purified by flash chromatography to obtain 2 grams of the title product as a solid. W. C. Still, et al., *Journal of Organic Chemistry*, 43:2923 (1978).

$^1$H NMR (CD$_3$SOCD$_3$): δ9.23 (s, 1 H), 7.87 (d, J=9 Hz, 1 H), 7.82 (s, 1 H), 7.78 (d, J=9 Hz, 1 H), 7.58 (dd, J=9, 9 Hz, 1 H), 7.46 (m, 1 H), 7.44 (d, J=9 Hz, 2 H), 7.32 (d, J=9 Hz, 2 H).

Analysis for C$_{15}$H$_{11}$ClN$_2$O$_4$S:
Theory: C, 51.36; H, 3.16; N, 7.99.
Found: C, 51.39; H, 3.25; N, 7.89.

Preparation 3

Preparation of
N-[[(4-methylphenyl)amino]carbonyl]-2-benzofuransulfonamide

2-Benzofuransulfonamide (7.6 mmol), prepared as described in Preparation 2, was reacted with 4-methylphenylisocyanate (7.6 mmol) as described in Preparation 2 to obtain 1.6 g of the title product as a solid.

$^1$H NMR (CD$_3$SOCD$_3$): δ8.91 (s, 1 H), 7.87 (d, J=8 Hz, 1 H), 7.81 (s, 1 H), 7.76 (d, J=8 Hz, 1 H), 7.57 (dd, J=8, 8 Hz, 1 H), 7.42 (dd, J=8, 8 Hz, 1 H), 7.28 (d, J=9 Hz, 2 H), 7.07 (d, J=9 Hz, 2 H), 2.23 (s, 3 H).

Analysis for C$_{16}$H$_{14}$N$_2$O$_4$S:
Theory: C, 58.70; H, 4.27; N, 8.48.
Found: C, 58.45; H, 4.33; N, 8.47.

Preparation 4

Preparation of
N-[[(3,4-dichlorophenyl)amino]carbonyl]-2-benzofuransulfonamide

2-Benzofuransulfonamide (7.6 mmol), prepared as described in Preparation 2, was reacted with 3,4-dichlorophenylisocyanate (7.6 mmol) as described in Preparation 2 to obtain 2.4 g of the title product as a solid.

$^1$H NMR (CD$_3$SOCD$_3$): δ9.43 (s, 1 H), 7.88 (d, J=8 Hz, 1 H), 7.85 (s, 1 H), 7.80 (m, 1 H), 7.76 (m, 1 H), 7.59 (dd, J=6, 8 Hz, 1 H), 7.52 (d. J=8 Hz, 1 H), 7.45 (dd, J=6, 8 Hz, 1 H), 7.35 (dd, J=3, 6 Hz, 1 H).

Analysis for C$_{15}$H$_{10}$Cl$_2$N$_2$O$_4$S:
Theory: C, 46.77; H, 2.63 ; N, 7.27.
Found: C, 46.78; H, 2.63; N, 7.24.

Preparation 5

Preparation of
N-[[(4-chlorophenyl)amino]carbonyl]-1H-indole-6-sulfonamide

To a solution of 4-chloro-3-nitrophenylsulfonamide (12 g, 51 mmol) dissolved in 50 ml of anhydrous dimethylformamide, was added 13.1 g (116 mmol) of ethylcyanoacetate and 10.5 g (76 mmol) of anhydrous potassium carbonate. This mixture was heated at 110° C. for 3 hours, cooled to room temperature, and added to ice water containing 8 ml of concentrated sulfuric acid. The mixture was extracted with ethyl acetate (3×200 ml), and the combined organic layer was back extracted with 200 ml of water. The organic layer was dried over anhydrous sodium sulfate, filtered, and concentrated under vacuum. Purification by a preparative high pressure liquid chromatogram (Waters Prep 500 A) with 55% ethyl acetate in hexanes on a silica gel cartridge. The product was added to 45 ml of 50% aqueous acetic acid containing 3 ml of concentrated sulfuric acid and refluxed for 12 hours. The reaction was cooled to room temperature and added to 400 ml water. This mixture was extracted with ethyl acetate (3×100 ml). The combined organic layer was dried with anhydrous sodium sulfate, filtered, and concentrated under vacuum. The residue was crystallized from 40 ml of ethyl acetate, 3 ml of ethanol and 1 ml of hexanes to obtain 6.9 g of 3-nitro-4-(2-acetonitrile)phenyl sulfonamide. This material was dissolved in 40 ml of ethanol containing 3 g of 5% palladium on activated carbon. This mixture was placed in a Parr Hydrogenation apparatus with 60 p.s.i. of hydrogen at 40° C. for 3 hours. This mixture was filtered, the filtrate concentrated under vacuum, and the residue recrystallized from 20 ml of ethyl acetate and 10 ml of ethanol to obtain 2.4 g of 6-indolesulfonamide. The sulfonamide (6.1 mmol) was reacted with 4-chlorophenylisocyanate (6.1 mmol) as described in Preparation 2 supra to obtain 1.1 g of the title product as a solid.

$^1$H NMR (CD$_3$SOCD$_3$): δ11.68 (s, 1 H), 8.90 (s, 1 H), 8.10 (d, J=2 Hz, 1 H), 7.72 (d, J=9 Hz, 1 H), 7.66 (d, J=3 Hz, 1 H), 7.58 (dd, J=3, 9 Hz, 1 H), 7.40 (d, J=9 Hz, 2 H), 7.28 (d, J=9 Hz, 2 H), 6.60 (d, J=2 Hz, 1 H).

Analysis for C$_{15}$H$_{12}$ClN$_3$O$_3$S:
Theory: C, 51.51; H, 3.46; N, 12.01.
Found: C, 51.24; H, 3.67; N, 11.72.

Preparation 6

Preparation of N-[[(4-chlorophenyl)amino]carbonyl]benzo[B]thiophene-2-sulfonamide To a solution of 13.4 g (100 mmol) of benzothiophene, dissolved in 50 ml anhydrous diethyl ether, was added 62.5 ml of a 1.6M hexanes solution of n-butyllithium (100 mmol). The reaction mixture was refluxed for 4 hours and then cooled to about −20° C. Sulfuryl chloride (16.1 ml, 200 mmol) was added dropwise. This suspension was stirred at ambient temperature overnight and then added to 75 ml of ice water. The ether layer was dried over anhydrous sodium sulfate, filtered, and concentrated under vacuum. The residue was added to 100 ml of concentrated ammonium hydroxide and the suspension was warmed to 55° C. The solution was diluted with 200 ml of water and stirred at ambient temperature for several hours. Product was collected by filtration under vacuum. The residue was suspended in 150 ml toluene and filtered to provide 9.2 g of 2-benzo[B]thiophenesulfonamide. The sulfonamide (25 mmol) was reacted with 4-chlorophenylisocyanate (27 mmol) as described in Preparation 2 above to obtain 8.7 g of the title product as a solid.

$^1$H NMR (CD$_3$SOCD$_3$): δ9.12 (s, 1 H), 8.22 (s, 1 H), 8.10 (m, 2H), 7.50 (m, 2 H), 7.44 (d, J=9 Hz, 2 H), 7.32 (d, J=9 Hz, 2 H).

Analysis for C$_{15}$H$_{11}$ClN$_2$O$_3$S$_2$:
Theory: C, 49.11; H, 3.02; N, 7.64.
Found: C, 49.36; H, 3.09; N, 7.54.

Preparation 7

Preparation of 3,4,5-trichlorobenzenesulfonamide 3,5-Dichloro-4-aminobenzenesulfonamide (12.1 g, 50.2 mmol) was added to 150 ml of concentrated hydrochloric acid; the thick suspension was cooled to 0° C. and, with vigorous stirring, treated with a solution of sodium nitrite (4.2 g, 60.9 mmol) in 20 ml of water, dropwise, over 15 min; the resulting orange diazonium salt mixture was slowly poured into a beaker containing cuprous chloride (12.4 g, 125.5 mmol) and 100 ml of concentrated hydrochloric acid at 0° C. (the reaction mixture foams and must be mechanically stirred). The stirred reaction mixture was warmed to room temperature for 1 h and then heated at 70° C. for 30 min. After cooling, the reaction mixture was extracted with methylene chloride (3×200 ml). The combined organic layers were dried over sodium sulfate, filtered and concentrated to give 9.89 g of the product as a yellow solid. Silica gel flash chromatography (30% ethyl acetate/hexane) afforded 8.13 g (62%) of the sulfonamide as a white solid.

Analysis of the product gave the following results:
mp=190–191° C.; R$_f$(1:1 EtOAc/hexane)=0.57; $^1$H NMR (300 MHz, d$_6$-DMSO) δ 7.68 (bs, 2H, exchanges with D$_2$O, NH$_2$) and 7.97 (s, 2H, Ar-H); IR(KBr) 3308, 2969, 1623, 1529, 1458, 1292, 1163, 1111, 976 and 842 cm$^{-1}$; FDMS(DMSO) m/e=259, 261, 263 (M+).

Analysis for C$_6$H$_4$Cl$_3$N$_1$O$_2$S$_1$:
Theory: C, 27.66; H, 1.55; N, 5.38.
Found: C, 27.87; H, 1.51; N, 5.09.

Preparation 8

Preparation of N-[[(4-chlorophenyl)amino]carbonyl]-3,4,5-trichlorobenzenesulfonamide The method of Preparation 2 was followed using 3,4,5-trichlorobenzenesulfonamide (2.6 g, 10 mmol) as prepared in Example 7, supra, 1N sodium hydroxide solution (10 ml, 10 mmol) and p-chlorophenyl isocyanate (1.7 g, 11 mmol) to yield 3.59 g (87%) of product.

Analysis of the product gave the following results:
mp=193–195° C.; R$_f$(5/95 MeOH/CH$_2$Cl$_2$)=0.24; $^1$H NMR (300 MHz, d$_6$-DMSO) δ 6.58 (s, 2H, exchanges with D$_2$O, NH$_2$), 7.31 (d, 2H, J=8.9 Hz, Ar-H), 7.37 (d, 2H, J=8.9 Hz, Ar-H) 7.73 (s, 2H, Ar-H), 9.09 (s, 1H, exchanges with D$_2$O, NH) and 10.7 (bs, 1H, exchanges with D$_2$O, NH); IR(KBr) 3496, 3470, 3375, 3294, 1700, 1622, 1595, 1524, 1451, 1401, 1341, 1166, 1041, 925 and 672 cm$^{-1}$; FDMS(DMSO) m/e 392, 394, 396 (M+).

Analysis for C$_{13}$H$_{10}$Cl$_3$N$_3$O$_3$S$_1$:
Theory: C, 39.56; H, 2.55; N, 10.65.
Found: C, 39.64; H, 2.55; N, 10.33.

Preparation 9

Preparation of N-[[(3,4-dichlorophenyl)amino]carbonyl]-2,3-dihydro-1-methyl-1H-indole-5-sulfonamide

Ethyl-indoline-1-carboxylate-5-sulfonamide

To a flask containing chlorosulfonic acid (125 ml, 1.9 moles) was added 70.5 grams of ethyl-indoline-1-carboxylate (0.37 mole) in portions under nitrogen purge with vigorous stirring over 20 minutes. The ethylindoline-1-carboxylate was prepared using techniques known in the art. See, e.g., B. de Oliveira, et al., *Journal of the Chemical Society, Perkin Transactions 1*, 1477 (1977). After 90 minutes at room temperature the reaction mixture was carefully poured onto 500 g crushed ice and extracted with dichloromethane (3×200 ml). The combined organic extracts were dried by filtration through calcium sulfate and then evaporated. The resulting crude sulfonyl chloride was stirred with 500 ml of ammonium hydroxide for 2 hours. Filtration, followed by washing (500 ml of water followed by 500 ml of diethyl ether) and vacuum drying gave the product sulfonamide as a white solid. Yield=80.4 g (81%).

Analysis of the product gave the following results:
mp=164–165° C.; R$_f$(1/1 ethyl acetate/hexanes)=0.28; $^1$H NMR (300 MHz, d$_6$-DMSO) δ 1.26 (t, 3H, J=7.1 Hz, CH$_2$CH$_3$), 3.13 (t, 2H, J=8.7 Hz, CH$_2$CH$_2$), 3.97 (t, 2H, J=8.7 Hz, CH$_2$CH$_2$), 4.19 (q, 2H, J=7.1 Hz, CH$_2$CH$_3$), 7.18 (s, 2H, exchanges with D$_2$O, SO$_2$NH$_2$), 7.61–7.63 (s,d, 2H, Ar-H) and 7.70 (bs, 1H, Ar-H); UV-(EtOH) λ$_{max}$(ε) 262.6 (20668), 208,6 (20726) and 204.6 (20527) nm; IR(KBr) 3326, 3229, 1693, 1489, 1325, 1186, 1046, 911, 828 and 768 cm$^{-1}$; FDMS(MeOH) m/e 270 (M+).

Analysis for C$_{11}$H$_{14}$N$_2$O$_4$S:
Theory: C, 48.88; H, 5.22; N, 10.36.
Found: C, 49.08; H, 5.40; N, 10.56.

N-methyl-indoline-5-sulfonamide

A 3-liter, 3-neck flask with mechanical stirrer and nitrogen purge line was charged with ethyl-indoline-1-carboxylate-5-sulfonamide (27 g, 100 mmoles), as prepared supra, and 1000 ml of anhydrous tetrahydrofuran. Under nitrogen purge was then added lithium aluminum hydride (95%, 10 g, 250 mmoles) in portions over 20 minutes, resulting in strong exotherms. The reaction was stirred at room temperature and monitored using HPLC (reverse-phase, 40/60/0.2% acetonitrile/water/phosphoric acid, 1 ml/min, monitoring at 254 nm). After 2 hours the mixture was cooled in an ice-bath and carefully quenched by the addition of ice until no further reaction was noted. Concentrated hydrochloric acid (65 ml) was next added until the pH equaled 3. The inorganic solids were removed by filtration and the filtrate evaporated to give a tan solid (23 g). Purification was effected by slurrying the crude solid in 250 ml of $H_2O$ for 30 minutes and filtering, followed by rinsing of the cake with $H_2O$ (300 ml) and diethyl ether (300 ml). Vacuum drying gave 17.3 g (81%) of product sulfonamide. Recrystallization from methanol gave an analytical sample.

Analysis of the product gave the following results: mp=176–177° C.; $R_f$(1/1 EtOAc/hexane)=0.29 ; $^1H$ NMR (300 MHz, $d_6$-DMSO) δ 2.74 (s 3H, $NCH_3$), 2.92 (t, 2H, J=8.4 Hz, $CH_2CH_2$), 3.38 (t, 2H, J=8.4 Hz, $CH_2CH_2$), 6.47 (d, 1H, J=8.3 Hz, Ar-H), 6.91 (bs, 2H, exchanges with $D_2O$, $SO_2NH_2$), 7.39 (s, 1H, Ar-H) and 7.44 (d, 1H, J=8.3 Hz, Ar-H); IR(KBr)3314, 3239, 1605, 1509, 1313, 1170 and 1062 $cm^{-1}$; FDMS(MeOH) m/e 212 ($M^+$).

Analysis for $C_9H_{12}N_2O_2S$:
Theory: C, 50.92; H, 5.70; N, 13.20.
Found: C, 50.87; H, 5.62; N, 12.91.

N-[[(3,4-dichlorophenyl)amino]carbonyl]-2,3-dihydro-1-methyl-1H-indole-5-sulfonamide To a solution of N-methyl-indoline-5-sulfonamide (16.0 g, 75 mmoles) in 75 ml of 1N aqueous sodium hydroxide and 75 ml of acetone was added, dropwise, a solution of 3,4-dichlorophenylisocyanate (97%, 14.6 g, 75.3 mmoles) in 70 ml of acetone over 10 minutes. Two hours later the mixture was filtered and the filtrate treated with 125 ml of 1N aqueous hydrochloric acid. The resulting solid was collected by filtration and rinsed with 100 ml of $H_2O$ and then slurried in 200 ml of ethanol/water (1/1) for 1 hour. Filtration, followed by washing (100 ml of ethanol followed by 200 ml of diethyl ether) and vacuum drying gave 19.7 grams of the purified title compound, a yield of 65%.

Analysis of the product gave the following results: mp=174–176° C.; $R_f$(1/9 MeOH/$CHCl_3$)=0.40 ; $^1H$ NMR (300 MHz, $d_6$-DMSO) δ 2.77(s, 3H, $NCH_3$), 2.96 (t, 2H, J=8.4 Hz, $CH_2CH_2$), 3.44 (t, 2H, J=8.4 Hz, $CH_2CH_2$), 6.48 (d, 1H, J=8.4 Hz, Ar-H), 7.25 (d, 1H, J=8.8 Hz, Ar-H), 7.46 (s, 1H, Ar-H), 7.49 (s, 1H, Ar-H), 7.58 (d, 1H, J=8.4 Hz, Ar-H), 7.58 (s, 1H, Ar-H), 8.96 (s, 1H, exchanges with $D_2O$, NH) and 10.57 (bs, 1H, exchanges with $D_2O$, $SO_2NH$); IR(KBr) 3352, 3274, 1710, 1610, 1525, 1458, 1322 and 1040 $cm^{-1}$; FDMS (MeOH) m/e 399, 401 ($M^+$).

Analysis for $C_{16}H_{15}Cl_2N_3O_3S$:
Theory: C, 48.01; H, 3.78; N, 10.50.
Found: C, 48.05; H, 3.92; N, 10.46.

Preparation 10

Preparation of
4-methyl-N-[[(4-trifluoromethylphenyl)amino]carbonyl]-benzenesulfonamide A solution of 8.0 g (49.65 mmoles) of 4-aminobenzotrifluoride in 10 ml of methylene chloride was added to a solution of 9.85 g (49.95 mmoles) of p-toluenesulfonyl isocyanate in 75 ml of methylene chloride with stirring. The mixture became quite warm and a heavy white precipitate formed. An additional 100 ml of methylene chloride were added. The reaction mixture was stirred an additional 15 minutes, and the precipitate was recovered by filtration affording 15.0 g of the title product as a white solid. A small amount of the material was crystallized from diethyl ether to provide the title compound (87% yield) with a melting point of 194–197° C.

Analysis for $C_{15}H_{13}F_3N_2O_3S$:
Theory: C, 50.25; H, 3.66; N, 7.82.
Found: C, 50.02; H, 3.63; N, 7.79.

Preparation 11

Preparation of
N[[(4-chlorophenyl)amino]carbonyl]-1,3-benzodioxole-5-sulfonamide Preparation of 1,3-benzodioxole-5-sulfonamide A 500 ml 3-neck round bottom flask was charged with 38.7 g (0.52 mole) of dimethylformamide. The contents of the flask were cooled to 0° C. After cooling, 70.18 g (0.52 mole) of sulfuryl chloride were added and the contents of the flask stirred for 10 minutes while maintaining the temperature at approximately 10° C.

After the Villsmeier reagent was formed, 60.16 g (0.5 mole) of 1,3-benzodioxole were added over a period of about 5 minutes. The mixture was heated to 80° C. for approximately 10 minutes. The temperature was increased to 110° C. and maintained for 5 minutes. The reaction mixture was allowed to cool to 40° C. and poured into a mixture of 450 g crushed ice, 200 ml water, and 200 ml of chloroform.

The resulting organic layer was decanted and then dripped into 200 ml of concentrated ammonium hydroxide. The solution was stirred for about 1.5 hours. After stirring, the organic and aqueous layers were allowed to separate and a yellow granular precipitate formed at the interface of the two layers. This solid was collected by filtration, washed with 100 ml of water, and dried overnight at 40° C. to provide 26.9 g of the desired subtitle intermediate.

Preparation of
N[[(4-chlorophenyl)amino]carbonyl]-1,3-benzodioxole-5-sulfonamide To a solution of 26.9 g of 1,3-benzodioxole-5-sulfonamide in 100 ml of acetone was added 150 ml of a 1N sodium hydroxide solution. A solution of 26.4 g of 4-chlorophenylisocyanate in 85 ml of acetone was added to the reaction mixture with stirring. After stirring at room temperature for 18 hours, the reaction mixture was filtered and 150 ml of 1N hydrochloric acid were added to the filtrate, thereby providing a precipitate. One liter of water was added, and the solid was recovered by filtration to provide the desired title product in 75% yield.

Preparation 12

Preparation of
N-[5-(2,3-dihydrobenzofuryl)sulfonyl]-N'-(3,4-dichlorophenyl)urea 2,3-Dihydrobenzofuran-5-sulfonamide This compound was prepared essentially according to the teachings of J. A. Aikins, et al., European Patent Publication 254,577, published Jan. 27, 1988. N,N-dimethylformamide (23.0 ml, 297 mmol) was cooled in an ice-salt bath and treated dropwise with sulfuryl chloride (20.0 g, 148 mmol) at such a rate that the reaction temperature was maintained below 15° C. To this was added 2.3-dihydrobenzofuran (17.0 g, 142 mmol), and after warming to room temperature, the reaction mixture was rapidly heated to 130° C. over ten minutes, and then allowed to cool to room temperature. The reaction mixture was poured into water/ice/dichloromethane, 1/5/1 (700 ml), and the organic layer collected. The aqueous layer was diluted with water (100 ml) and extracted with dichloromethane. The combined organic phase was dripped into an ammonium hydroxide solution (3N, 250 ml), and allowed to stir overnight. Residual dichloromethane was removed by distillation and the resulting solid collected on a filter, washed with a small amount of water, followed by ether and then dried by aspiration to provide 12.8 g (45%) of the product.

Analysis of the product gave the following results: mp=163-164.5° C.; $^1$H NMR (300 MHz, d$_6$-DMSO) δ 3.21 (t, 2H, J=8.8 Hz, CH$_2$), 4.60 (t, 2H, J=8.8 Hz, CH$_2$), 6.86 (d, 1H, J=8.4 Hz, Ar-H), 7.12 (bs, 2H, exchanges with D$_2$O, SO$_2$NH$_2$), 7.56 (d, 1H, J=8.4 Hz, Ar-H), 7.64 (s, 1H, Ar-H); IR(KBr) 3356, 3255, 1606, 1590, 1557, 1407, 1442, 1314, 1249, 1149, 1116, 1070, 982, 923 and 836 cm$^{-1}$; FDMS (MeOH) m/e 200 (M+).

Analysis for C$_8$H$_9$NO$_3$S:
Theory: C, 48.23; H, 4.55; N, 7.03; S, 16.09.
Found: C, 48.01; H, 4.71; N, 7.00; S, 16.36.

N-[5-(2,3-dihydrobenzofuryl)sulfonyl]-N'-(3,4-dichlorophenyl)urea

A solution of the product of Example 1 (29.6 g, 148.6 mmol) in acetone (75 ml) and 1N aqueous NaOH (150 ml, 150 mmol) was treated dropwise with a solution of 3,4-dichlorophenylisocyanate (30.0 g, 154.8 mmol) in 75 ml of acetone over 20 minutes. After stirring two hours, the insoluble bis(3,4-dichlorophenyl)urea was removed by filtration and the resulting clear solution neutralized by the addition of 1N aqueous HCl (150 ml, 150 mmol). The slurry was stirred 30 minutes, filtered and washed with water (500 ml), ether (200 ml), ether/hexane (1/1, 100 ml) and hexane (200 ml). Vacuum drying gave 50.1 g of crude product which was slurried in ethanol (300 ml) for one hour, collected on a filter and washed with ether. This ethanol reslurry was repeated and provided 42.7 g (74%) of the title compound after vacuum drying (50° C.).

Analysis of the product gave the following results: mp=188-189° C.; $^1$H NMR (300 MHz, d$_6$-DMSO) δ 3.25 (t, 2H, J=8.8 Hz, CH$_2$), 4.63 (t, 2H, J=8.8 Hz, CH$_2$). 6.92 (d, 1H, J=8.6 Hz, Ar-CH$_2$), 7.25 (dd, 1H, J=2.5, 8.8 Hz, Ar-H), 7.48 (d, 1H, J=8.8 Hz, Ar-H), 7.68 (d, 1H, J=2.5 Hz, Ar-H), 7.71 (d, 1H, J=8.5 Hz, Ar-H), 7.77 (s, 1H, Ar-H), 9.08 (s, 1H, exchanges with D$_2$O, ArNH), 10.85, (bs, 1H, exchanges with D$_2$O, SO$_2$NH); IR(KBr) 3275, 1701, 1580, 1511, 1452, 1380, 12444, 1202, 1142, 1115, 1045, 896, 708 and 585 cm$^{-1}$; FDMS (MeOH) m/e 386, 388, 390 (M+).

Analysis for C$_{15}$H$_{12}$Cl$_2$N$_2$O$_4$S:
Theory: C, 46.53; H, 3.12; N, 7.23.
Found: C, 46.77; H, 3.24; N, 7.26.

Preparation 13

Preparation of
N-[[(4-chlorophenyl)amino]carbonyl]-4-methylbenzenesulfonamide

A solution of 6.25 g (49.00 mmoles) of 4-chloroaniline in 10 ml of methylene chloride was added to a solution of 9.85 g (49.95 mmoles) of p-toluenesulfonyl isocyanate in 75 ml of methylene chloride with stirring. The mixture became quite warm and a heavy white precipitate formed. An additional 100 ml of methylene chloride were added. The reaction mixture was stirred an additional 15 minutes, and the precipitate was recovered by filtration affording 15.0 g of the title product as a white solid. A small amount of the material was crystallized from diethyl ether to provide the title compound (87% yield) with a melting point of 174-176° C.

Analysis for C$_{14}$H$_{13}$ClN$_2$O$_3$S:
Theory: C, 51.77; H, 4.03; N, 8.63.
Found: C, 51.90; H, 4.08; N, 8.67.

EXAMPLE 1

1-(4-methylphenylsulfonyl)-3-(4-chlorophenyl)-4,5-dihydroxy-4-methyl-imidazolidin-2-one

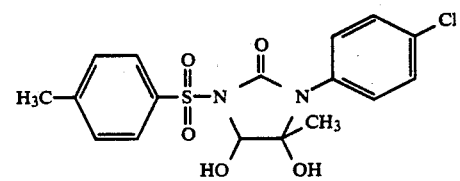

The title compound was prepared essentially as described in T. L. Hough, et al., Journal of Heterocyclic Chemistry, 23:1125-1130 (1986). To a mixture of 2.0 g (6.16 mmoles) of the compound as prepared in Preparation 13 in 35 ml of ethanol was added 10 ml of an aqueous pyruvaldehyde solution (40% by weight, 4.4 g, 61 mmoles pyruvaldehyde). The mixture was then adjusted to pH 7.4 using 12 ml of 2N sodium hydroxide. The reaction mixture was then stirred under a nitrogen atmosphere for about 1.5 hours. The reaction mixture was then concentrated under vacuum to afford a dark brown oil. This oil was purified by silica gel chromatography and product eluted with 40% ethyl acetate in hexane. Removal of solvent from product-containing fractions afforded 1.9 g of an oil which was taken up on 40% ethyl acetate in hexane. Addition of hexane caused the formation of a white precipitate. When the solvent was decanted off a yellow oil remained. This oil was taken up in chloroform and the chloroform removed in vacuo to afford 1.1 g of product as a light yellow powder. NMR analysis of this powder was consistent with the structure proposed for the title compound. m.p. 60-70° C.

Analysis for C$_{19}$H$_{19}$ClN$_2$O$_5$S:
Theory: C, 51.45; H, 4.32; N, 7.06.
Found: C, 51.78; H, 4.94; N, 5.86.

Preparation 14

Preparation of
N-[[(4-chlorophenyl)amino]carbonyl]-indan-5-sulfonamide

To a mixture of 93.2 g of indane-5-sulfonamide in 300 ml of acetone were added 490 ml of 1N sodium hydroxide. A solution of 79.36 g of 4-chlorophenylisocyanate in 250 ml of acetone was added to the reaction mixture with stirring. After stirring at room temperature for about 18 hours, the reaction mixture was filtered and 490 ml of 1N hydrochloric acid were added to the filtrate, thereby providing a fine white precipitate. One liter of water was added, and the solid was recovered by filtration to provide 144.86 g of the desired title product. m.p. 169-172° C.
Analysis for $C_{16}H_{15}ClN_2O_3S$:
Theory: C, 54.78; H, 4.31; N, 7.79.
Found: C, 54.95; H, 4.43; N, 7.94.

EXAMPLE 2

1-(indan-5-yl-sulfonyl)-3-(4-chlorophenyl)-4,5-dihydroxy-4-methyl-imidazolidin-2-one

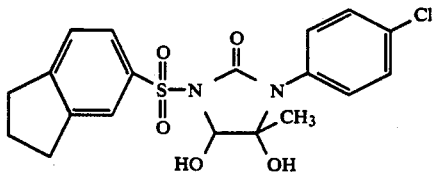

The title compound was prepared essentially as described in T. L. Hough, et al., *Journal of Heterocyclic Chemistry*, 23:1125-1130 (1986). To a mixture of 1.71 g of the compound as prepared in Preparation 14, in 35 ml of ethanol, was added 8.2 ml of an aqueous solution of pyruvaldehyde (40% by weight, 3.6 g, 50 mmoles pyruvaldehyde). The mixture was then adjusted to pH 7.6 with 1N sodium hydroxide and allowed to stir under a nitrogen atomsphere for 3.5 hours. Concentration in vacuo afforded a dark brown oil. This was taken up in ethyl acetate and purified by silica gel chromatography. Product-containing fractions were eluted with 60% ethyl acetate in hexane. The yellow oil obtained on removal of solvent was dissolved in 50% ethyl acetate in hexane, and hexane added, resulting in a white precipitate. Hexane was added until no more precipitate formed. The solvent was decanted from the precipitate, which became an oil. This was taken up in chloroform and the chloroform removed under vacuum to leave 0.77 g of a flaky yellow solid. NMR analysis of this solid was consistent with the structure proposed for the title compound. m.p. 59-70.

The compounds of Formula I are antineoplastic agents. Thus, the invention also provides a method of treating a susceptible neoplasm in a mammal which comprises administering to a mammal in need of said treatment an oncolytically effective amount of a compound of Formula I. In particular, the present compounds are believed to be useful in treating solid tumors including carcinomas such as ovarian, non-small cell lung, gastric, pancreatic, prostate, renal cell, breast, colorectal, small cell lung, melanoma, and head and neck; and sarcomas such as Kaposi's sarcoma and rhabdomyosarcoma.

The compounds of Formula I have been shown to be active against transplanted mouse tumors in vivo. The compounds were tested in C3H mice bearing a 6C3HED lymphosarcoma, also known as the Gardner lymphosarcoma (GLS). The 6C3HED lymphosarcoma was obtained from the Division of Cancer Treatment, National Cancer Institute, Tumor Bank, maintained at E. G. and G. Mason Research (Worcester, Mass.).

First passage tumor was stored in liquid nitrogen using standard techniques. The transplanted tumor was reestablished from the Tumor Bank every six months or as needed. The tumor was maintained by serial passage twice weekly in C3H mice.

In the procedures utilized here, the tumor was removed from passage animals and minced into 1- to 3-mm cubic fragments using sterile techniques. Tumor pieces were checked for sterility using both Antibiotic Medium 1 and Brain Heart Infusion (Difco, Detroit, Mich.). The tumor pieces were implanted into the recipient C3H mice subcutaneously in an auxillary site by trochar.

Drug therapy on the appropriate schedule was initiated seven days after tumor implantation. The compound being tested was mixed with 2.5% Emulphor EL620 from GAF Corporation (1:40 dilution in 0.9% saline). The total dosage volume for each administration was 0.5 ml. All animals were weighed at the beginning and end of administration of the subject compounds. Food and water were provided ad libitum.

Each control group and each dosage level of the treated groups generally consisted of 10 mice selected at random from the pool of implanted animals. The formulations were administered orally by gavage with the use of an 18-gauge needle. Compounds were dosed daily for 10 days.

The tumor was measured five days after treatment ended with two dimensional measurements (width and length) of the tumor taken using digital electronic calipers interfaced to a microcomputer. J. F. Worzalla, et al., *Investigational New Drugs*, 8:241-251 (1990). Tumor weights were calculated from these measurements using the following formula:

$$\text{Tumor weight (mg)} = \frac{\text{tumor length (mm)} \times [\text{tumor width (mm)}]^2}{2}$$

At least one control group of an equal number of mice was treated with the same volume of 2.5% Emulphor only. The percent inhibition was determined by subtracting the ratio of the mean tumor size of the test group relative to the control group from one and multiplying the result by 100.

The results of several experiments in mice bearing the 6C3HED lymphosarcoma when the instant compounds were administered orally are provided in the following table. In this table, column 1 gives the example number of the compound of Formula I administered; column 2 gives the dosage level of the compound in milligrams per kilogram of body weight; column 3 describes the percent inhibition of tumor growth; and column 4 tallies the number of mice which died during the course of the experiment relative to the total number of animals in the group.

TABLE

In Vivo Activity of the Some of the Compounds of Formula I Against the 6C3HED Lymphosarcoma

| Example No. | Dosage | Percent Inhibition | Toxic/Total |
|---|---|---|---|
| 1 | 300 | 98 | 0/10 |
|  | 150 | 75 | 0/10 |
| 2 | 300 | 76 | 6/10 |
|  | 150 | 55 | 0/10 |

The compounds of Formula I are usually administered in the form of pharmaceutical compositions. These compounds can be administered by a variety of routes including oral, rectal, transdermal, subcutaneous, intravenous, intramuscular, and intranasal. The Formula I compounds are preferably administered in the form of oral pharmaceutical compositions. Such compositions are prepared in a manner well known in the pharmaceutical art and comprise at least one active compound.

The present invention also includes pharmaceutical compositions which contain, as the active ingredient, the compounds of Formula II associated with one or more pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compound is usually effective over a wide dosage range. For example, dosages per day normally fall within the range of about 0.5 to about 600 mg/kg of body weight. In the treatment of adult humans, the range of about 1 to about 50 mg/kg, in single or divided dose, is preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms. Therefore the above dosage ranges are not intended to limit the scope of the invention in any way.

FORMULATION EXAMPLE 1

Hard gelatin capsules containing the following ingredients are prepared:

| Ingredient | Quantity (mg/capsule) |
| --- | --- |
| 1-(4-methylphenylsulfonyl)-3-(4-chlorophenyl)-4,5-dihydroxy-4-methyl-imidazolidin-2-one | 250.0 |
| Starch | 305.0 |
| Magnesium stearate | 5.0 |

The above ingredients are mixed and filled into hard gelatin capsules in 560 mg quantities.

FORMULATION EXAMPLE 2

A tablet formula is prepared using the ingredients below:

| Ingredient | Quantity (mg/tablet) |
| --- | --- |
| 1-(2,3-dihydrobenzofur-5-yl-sulfonyl)-3-(3,4-dichlorophenyl)-4,5-dihydroxy-4-methyl-imidazolidin-2-one | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

FORMULATION EXAMPLE 3

A dry powder inhaler formulation is prepared containing the following components:

| Ingredient | Weight % |
| --- | --- |
| 1-(3,4,5-trichlorophenylsulfonyl)-3-(3,4-dibromophenyl)-4,5-dihydroxy-4-methyl-imidazolidin-2-one | 5 |
| Lactose | 95 |

The active mixture is mixed with the lactose and the mixture is added to a dry powder inhaling appliance.

FORMULATION EXAMPLE 4

Tablets, each containing 60 mg of active ingredient, are prepared as follows:

| Ingredient | Quantity (mg/tablet) |
| --- | --- |
| 1-(inden-5-yl-sulfonyl)-3-(4-trifluoromethylphenyl)-4,5-dihydroxy-4-methyl-imidazolidin-2-one | 60.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 150 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 80 mg of medicament are made as follows:

| Ingredient | Quantity (mg/capsule) |
| --- | --- |
| 1-(1-methylindolin-5-yl-sulfonyl)-3-(4-methylphenyl)-4,5-dihydroxy-4-methyl-imidazolidin-2-one | 80.0 mg |
| Starch | 109.0 mg |
| Magnesium stearate | 1.0 mg |
| Total | 190.0 mg |

The active ingredient, cellulose, starch, and magnesium stearate are blended, passed through a No. 20 mesh U.S. sieve, and filled into hard gelatin capsules in 190 mg quantities.

FORMULATION EXAMPLE 6

Suppositories, each containing 225 mg of active ingredient are made as follows:

| Ingredient | Amount |
| --- | --- |
| 1-(benzothiophen-6-yl-sulfonyl)-3-(4-methylphenyl)-4,5-dihydroxy-4-methyl-imidazolidin-2-one | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
| --- | --- |
| 1-(1,3-benzodioxol-5-yl-sulfonyl)-3-(4-methylphenyl)-4,5-dihydroxy-4-methyl-imidazolidin-2-one | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor | q.v. |
| Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules, each containing 150 mg of medicament, are made as follows:

| Ingredient | Quantity (mg/capsule) |
| --- | --- |
| 1-(1,3-dihydro-1,4-benzodioxin-6-yl-sulfonyl)-3-(4-methylphenyl)-4,5-dihydroxy-4-methyl-imidazolidin-2-one | 150.0 mg |
| Starch | 407.0 mg |
| Magnesium stearate | 3.0 mg |
| Total | 560.0 mg |

The active ingredient, cellulose, starch, and magnesium stearate are blended, passed through a No. 20 mesh U.S. sieve, and filled into hard gelatin capsules in 560 mg quantities.

We claim:

1. A compound of the formula

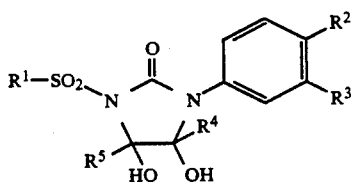

wherein: $R^1$ is selected from the group consisting of

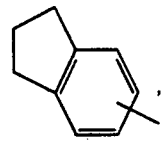

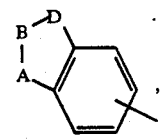

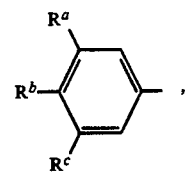

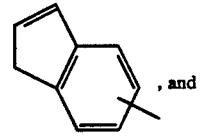

, and wherein
E is nitrogen, sulfur, or oxygen;

wherein A is —O—, —S(O)$_n$—, —CH$_2$S(O)$_n$—, —NR—, —CH$_2$—, —CH$_2$CH$_2$—, or —CH$_2$O—;
D is —CH$_2$—, —S(O)$_n$13, —NR—, —CH$_2$S(O)$_n$—, or —O—;
B is —CH$_2$—, —O—, —S(O)$_n$—, or —NR—;
R is methyl or ethyl;
n is 0-2;

provided that at least one of A, B, and D is not —S(O)$_n$— or —CH$_2$S(O)$_n$—; and R$^a$, R$^b$, and R$^c$ are independently selected from the group consisting of hydrogen, halo, C$_1$-C$_3$ alkyl, C$_1$-C$_3$ alkoxy, and trifluoromethyl;

R$^4$ and R$^5$ are independently selected from the group consisting of hydrogen and C$_1$-C$_3$ alkyl;

R$^3$ is hydrogen, halo, C$_1$-C$_3$ alkyl, or trifluoromethyl; and

R$^2$ is halo, C$_1$-C$_3$ alkyl, or trifluoromethyl; or a pharmaceutically acceptable salt or solvate thereof.

2. A compound as claimed in claim 1 wherein R$^2$ is halo.

3. A compound as claimed in claim 2 wherein R$^1$ is indanyl.

4. A compound as claimed in claim 2 wherein R$^1$ is 2,3-dihydrobenzofuryl.

5. A compound as claimed in claim 2 wherein R$^1$ is substituted phenyl.

6. A method of treating a susceptible neoplasm in a mammal which comprises administering to a mammal in need of said treatment an oncolytically effective amount of a compound of the formula

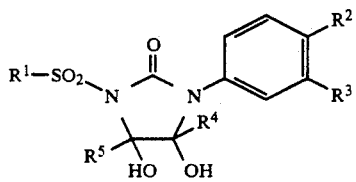

wherein: R$^1$ is selected from the group consisting of

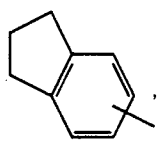

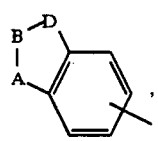

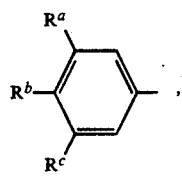

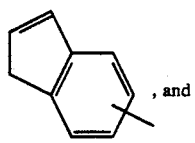, and

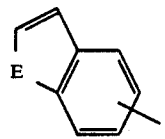

wherein
E is nitrogen, sulfur, or oxygen;
wherein A is —O—, —S(O)$_n$—, —CH$_2$S(O)$_n$—, —NR—, —CH$_2$—, —CH$_2$CH$_2$—, or —CH$_2$O—;
D is —CH$_2$—, —S(O)$_n$—, —NR—, —CH$_2$S(O)$_n$—, or —O—;
B is —CH$_2$—, —O—, —S(O)$_n$—, or —NR—;
R is methyl or ethyl;
n is 0-2;

provided that at least one of A, B, and D is not —S(O)$_n$— or —CH$_2$S(O)$_n$—; and R$^a$, R$^b$, and R$^c$ are independently selected from the group consisting of hydrogen, halo, C$_1$-C$_3$ alkyl, C$_1$-C$_3$ alkoxy, and trifluoromethyl;

R$^4$ and R$^5$ are independently selected from the group consisting of hydrogen and C$_1$-C$_3$ alkyl;

R$^3$ is hydrogen, halo, C$_1$-C$_3$ alkyl, or trifluoromethyl; and

R$^2$ is halo, C$_1$-C$_3$ alkyl, or trifluoromethyl; or a pharmaceutically acceptable salt or solvate thereof.

7. A method as claimed in claim 6 employing a compound wherein R$^2$ is halo.

8. A method as claimed in claim 7 employing a compound wherein R$^1$ is indanyl.

9. A method as claimed in claim 7 employing a compound wherein R$^1$ is 2,3-dihydrobenzofuryl.

10. A method as claimed in claim 7 employing a compound wherein R$^1$ is substituted phenyl.

11. A pharmaceutical formulation comprising an effective amount of a compound of the formula

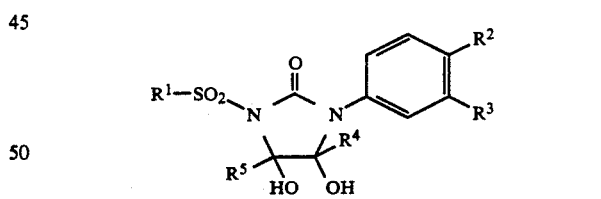

wherein: R$^1$ is selected from the group consisting of

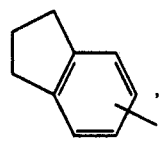

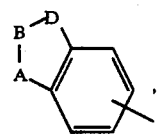

-continued

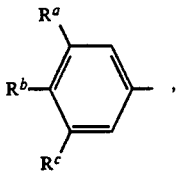

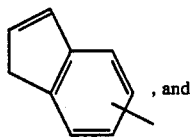, and

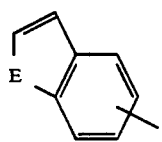

wherein

E is nitrogen, sulfur, or oxygen;

wherein A is —O—, —S(O)$_n$—, —CH$_2$S(O)$_n$—, —NR—, —CH$_2$—, —CH$_2$CH$_2$—, or —CH$_2$O—;

D is —CH$_2$—, —S(O)$_n$—, —NR—, —CH$_2$S(O)$_n$—, or —O—;

B is —CH$_2$—, —O—, —S(O)$_n$—, or —NR—;

R is methyl or ethyl;

n is 0-2;

provided that at least one of A, B, and D is not —S(O)$_n$— or —CH$_2$S(O)$_n$—; and R$^a$, R$^b$, and R$^c$ are independently selected from the group consisting of hydrogen, halo, C$_1$-C$_3$ alkyl, C$_1$-C$_3$ alkoxy, and trifluoromethyl;

R$^4$ and R$^5$ are independently selected from the group consisting of hydrogen and C$_1$-C$_3$ alkyl;

R$^3$ is hydrogen, halo, C$_1$-C$_3$ alkyl, or trifluoromethyl; and

R$^2$ is halo, C$_1$-C$_3$ alkyl, or trifluoromethyl; or a pharmaceutically acceptable salt or solvate thereof.

12. A formulation as claimed in claim 11 employing a compound wherein R$^2$ is halo.

13. A formulation as claimed in claim 11 employing a compound wherein R$^1$ is indanyl.

14. A formulation as claimed in claim 12 wherein R$^1$ is 2,3-dihydrobenzofuryl.

15. A formulation as claimed in claim 12 wherein R$^1$ is substituted phenyl.

* * * * *